United States Patent [19]

Eidenschink et al.

[11] Patent Number: 4,572,794

[45] Date of Patent: Feb. 25, 1986

[54] ACETONITRILES, THEIR PREPARATION, AND DIELECTRICS AND ELECTRO-OPTICAL DISPLAY ELEMENTS CONTAINING THEM

[75] Inventors: Rudolf Eidenschink, Dieburg; Georg Weber, Erzhausen, both of Fed. Rep. of Germany

[73] Assignee: Merck Patent Gesellschaft mit beschränkter Haftung, Darmstadt, Fed. Rep. of Germany

[21] Appl. No.: 453,047

[22] Filed: Dec. 27, 1982

[30] Foreign Application Priority Data

Dec. 24, 1981 [DE] Fed. Rep. of Germany ....... 3151367

[51] Int. Cl.$^4$ .......................... G02F 1/13; C09K 3/34
[52] U.S. Cl. .............................. 252/299.2; 252/299.5; 252/299.63; 252/299.66; 260/465 R; 260/465 C; 260/465 D; 260/465 F; 260/464; 350/350 R
[58] Field of Search ........... 252/299.63, 299.5, 299.66, 252/299.2; 260/465 D, 465 F, 465 C, 464, 465 R; 350/350 R

[56] References Cited

U.S. PATENT DOCUMENTS

| | | | |
|---|---|---|---|
| 3,240,722 | 3/1966 | Orttung et al. | 260/465 D |
| 3,947,375 | 3/1976 | Gray et al. | 252/299.66 |
| 3,983,049 | 9/1976 | Aftergut et al. | 252/299.5 |
| 4,130,502 | 12/1978 | Eidenschink et al. | 252/299.63 |
| 4,154,697 | 5/1979 | Eidenschink et al. | 252/299.63 |
| 4,181,625 | 1/1980 | Eidenschink et al. | 252/299.63 |
| 4,293,193 | 10/1981 | Labes et al. | 252/299.5 |
| 4,344,856 | 8/1982 | Demus et al. | 252/299.61 |
| 4,348,324 | 9/1982 | Demus et al. | 252/299.61 |
| 4,410,445 | 10/1983 | Baur et al. | 350/350 R |

FOREIGN PATENT DOCUMENTS 2636684  2/1978  Fed. Rep. of Germany ... 252/299.5

OTHER PUBLICATIONS

Dabrowski, R., et al., Mol. Cryst. Liq. Cryst., vol 87, pp. 109-135 (Jun. 1982).
C. A., 96(13) 103527p (Mar. 1982).
C. A., 96(12) 95420f (Mar. 1982).
Demus, D., Nonemissive Electrooptic Displays, pp. 83-119 (1975).
Dabrowski, R., et al., Biul. Wojsk. Akad. Tech., vol. 30(6), pp. 143-175 (1981).

*Primary Examiner*—Teddy S. Gron
*Attorney, Agent, or Firm*—Millen & White

[57] ABSTRACT

Acetonitriles of Formula I

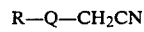

R—Q—CH$_2$CN   I wherein R is alkyl, alkoxy or alkanoyloxy, each of up to 8 carbon atoms, and Q is 2, 3 or 4 phenylene and/or cyclohexylene groups, each bonded to one another in the 1,4-position, exhibit good solvent properties for ionic dopants and are valuable components of liquid-crystalline dielectrics.

14 Claims, No Drawings

ACETONITRILES, THEIR PREPARATION, AND DIELECTRICS AND ELECTRO-OPTICAL DISPLAY ELEMENTS CONTAINING THEM

BACKGROUND OF THE INVENTION

The determining factor for the shape of the contrast voltage characteristic of a display element based on the dynamic scattering effect, is the anisotropy of the conductivity, which can be brought about by dissolving a conducting salt in the dielectric of the electro-optical cell. The solubility of the conducting salts is frequently a source of difficulty with respect to the stability of the displays on storage at low temperatures.

SUMMARY OF THE INVENTION

Accordingly, it is an object of this invention to provide new liquid-crystalline compounds which are suitable as components of liquid-crystalline dielectrics and, in particular, which increase the conductivity of those dielectrics which contain conducting salts, and, moreover, which increase storability.

Upon further study of the specification and appended claims, further objects and advantages of this invention will become apparent to those skilled in the art.

These objects have been achieved by this invention by providing new acetonitriles of Formula I

R—Q—CH$_2$CN      I wherein R is alkyl, alkoxy or alkanoyloxy each of up to 8 carbon atoms, and Q is 2, 3 or 4 phenylene and/or cyclohexylene groups each bonded to one another in the 1,4 position.

DETAILED DISCUSSION

The compounds of this invention can be used analogously to similar compounds, for example those disclosed in U.S. Pat. No. 4,130,502, equivalent to German Offenlegungsschrift No. 2,636,684, whose disclosures are incorporated by reference herein, as components of liquid-crystalline dielectrics, in particular for displays which are based on the principle of dynamic scattering.

It has been found that the acetonitriles of Formula I are excellently suitable as components of liquid-crystalline dielectrics. In particular, using them, liquid-crystalline phases can be produced having relatively high optical anisotropy and a very good dissolving capacity for ionic doping materials, for example, conducting salts. The addition of these compounds to liquid-crystalline dielectrics which contain conducting salts, increases their dissociation and thus the conductivity of the dielectric.

In addition, the compounds of Formula I have an extremely extensive range of use. Depending on the selection of the substituents, these compounds can serve as base materials of which liquid-crystalline dielectrics are chiefly composed. Furthermore, compounds of Formula I can also be added to liquid-crystalline base materials of other classes of compounds, in smaller proportions of, for example, 2 to 25 percent by weight, in order to affect the value of the mean dielectric constant of a dielectric of this type.

The compounds of Formula I are colorless in the pure state and form liquid-crystalline mesophases in a temperature range which is favorable for electro-optical use.

The present invention thus relates to the acetonitriles of Formula I, processes for their preparation and their use as components of liquid-crystalline dielectrics. In addition, the invention relates to liquid-crystalline dielectrics containing at least one acetonitrile of Formula I and electro-optical display elements based on a liquid-crystal cell which contains a liquid-crystalline dielectric of this type.

The acetonitriles of Formula I according to the invention comprise, in particular, the preferred 4-cyclohexylphenylacetonitriles of Formula Ia, biphenyl-4-ylacetonitriles of Formula Ib and 4'-cyclohexylbiphenyl-4-ylacetonitriles of Formula Ic

| | |
|---|---|
| R—Cy—Ph—CH$_2$CN | Ia |
| R—Ph—Ph—CH$_2$CN | Ib |
| R—Cy—Ph—Ph—CH$_2$CN | Ic | wherein Cy, in each case, is a 1,4-cyclohexylene radical and Ph, in each case, is a 1,4-phenylene radical.

In addition, Formula I preferably includes the phenylacetonitrile derivatives of Formulae Id to In

| | |
|---|---|
| R—Ph—Ph—Ph—CH$_2$CN | Id |
| R—Ph—Cy—Ph—CH$_2$CN | Ie |
| R—Cy—Cy—Ph—CH$_2$CN | If |
| R—PH—Ph—Ph—Ph—CH$_2$CN | Ig |
| R—Ph—Ph—Cy—Ph—CH$_2$CN | Ih |
| R—Ph—Cy—Ph—Ph—CH$_2$CN | Ii |
| R—Ph—Cy—Cy—Ph—CH$_2$CN | Ij |
| R—Cy—Ph—Ph—Ph—CH$_2$CN | Ik |
| R—Cy—Ph—Cy—Ph—CH$_2$CN | Il |
| R—Cy—Cy—Ph—Ph—CH$_2$CN | Im |
| R—Cy—Cy—Cy—Ph—CH$_2$CN | In | as well as the cyclohexylacetonitriles of Formulae Iaa to Inn

| | |
|---|---|
| R—Cy—Cy—CH$_2$CN | Iaa |
| R—Ph—Cy—CH$_2$CN | Ibb |
| R—Cy—Ph—Cy—CH$_2$CN | Icc |
| R—Ph—Ph—Cy—CH$_2$CN | Idd |
| R—Ph—Cy—Cy—CH$_2$CN | Iee |
| R—Cy—Cy—Cy—CH$_2$CN | Iff |
| R—Ph—Ph—Ph—Cy—CH$_2$CN | Igg |
| R—Ph—Ph—Cy—Cy—CH$_2$CN | Ihh |
| R—Ph—Cy—Ph—Cy—CH$_2$CN | Iii |
| R—Ph—Cy—Cy—Cy—CH$_2$CN | Ijj |
| R—Cy—Ph—Ph—Cy—CH$_2$CN | Ikk |
| R—Cy—Ph—Cy—Cy—CH$_2$CN | Ill |

R—Cy—Cy—Ph—Cy—CH$_2$CN    Imm

R—Cy—Cy—Cy—Cy—CH$_2$CN    Inn wherein R, Cy and Ph are as defined above.

In the compounds of Formula I, Ia to In and Iaa to Inn which contain cyclohexylene radicals, those stereoisomers are preferred in which the two 1,4 substituents each are in the trans-position relative to one another.

In the compounds of Formula I, the radical R is preferably straight-chained, and, thus, is preferably methyl, ethyl, n-propyl, n-butyl, n-pentyl, n-hexyl, n-heptyl, n-octyl, methoxy, ethoxy, n-propyloxy, n-butyloxy, n-pentyloxy, n-heptyloxy, n-octyloxy, formyloxy, acetoxy, propionyloxy, butyryloxy, pentanoyloxy, hexanoyloxy, heptanoyloxy or octanoyloxy.

Compounds of Formula I having a branched wing group R can occasionally be of importance, due to a better solubility in the customary liquid-crystalline base materials; but they are particularly important as chiral doping materials when they have optical activity due to the chain branching. Branched groups R as a rule do not contain more than one chain branching. Preferred branched radicals R are isopropyl, 2-methylpropyl, 2-methylbutyl, 3-methylbutyl, 2-methylpentyl, 3-methylpentyl, 2-ethylhexyl, 1-methylhexyl, 1-methylheptyl, isopropyloxy, 2-methylpropyloxy, 2-methylbutyloxy, 3-methylbutyloxy, 2-methylpentyloxy, 3-methylpentyloxy, 2-ethylhexyloxy, 1-methylhexyloxy, 1-methylheptyloxy, isobutyryloxy, 2-methylbutyryloxy, 3-methylbutyryloxy, 3-ethylbutyryloxy, 2-ethylbutyryloxy, 2-, 3- or 4-methylpentanoyloxy, 2- or 3-ethylpentanoyloxy.

All groups R contain 1-8, preferably 3-5 C atoms. The alkyl groups are preferred to the alkoxy and the alkanoyloxy groups.

Furthermore, the compounds of Formula I are prepared by methods known per se, as are described in the literature (for example in the standard works, such as Houben-Weyl, Methoden der Organischen Chemie (Methods of Organic Chemistry), Georg-Thieme-Verlag, Stuttgart), namely under reaction conditions which are known and suitable for the reactions indicated. For this purpose, variants which are known per se but which are not mentioned in more detail here can also be used.

The starting materials can also be formed in situ, if desired, in such a manner that they are not isolated from the reaction mixture but are immediately reacted further to give the compounds of Formula I. For example, the acetonitriles of Formula I can be prepared by treating an acetamide of Formula II

R—Q—CH$_2$CONH$_2$    II wherein Q and R are as defined above with an agent which splits off water, or reacting a halogenomethyl compound of Formula III R—Q—CH$_2$Hal    III wherein Hal is Cl, Br or I and Q and R are as defined above with a metal cyanide.

Preferably, the compounds of Formula I are prepared by dehydration of the corresponding acetamides of Formula II. Examples of suitable agents for splitting off water include inorganic acid chlorides, such as SOCl$_2$, PCl$_3$, PCl$_5$, SO$_2$Cl$_2$, COCl$_2$, also P$_2$O$_5$, P$_2$S$_5$, AlCl$_3$ as a double compound with NaCl, and aromatic sulfonic acids and sulfonyl halides. The reaction can be carried out in the presence or absence of an inert solvent, for example an aromatic hydrocarbon, such as benzene, toluene, or xylene, preferably at temperatures of about 50° to 150°.

The acetonitriles of Formula I can also be obtained by reaction of appropriate chlorine, bromine or iodine compounds of Formula III with metal cyanides, preferably NaCN, KCN or Cu$_2$(CN)$_2$, preferably in the presence of an inert solvent, such as dimethylformamide or dimethyl sulfoxide at temperatures of about 20° to about 150°.

The starting materials of Formulae II and III are largely new. However, they can be prepared by methods which are also known per se. Thus, the acetamides of Formula II can be obtained by reaction of the corresponding methyl ketones of the formula R—Q—COCH$_3$ with morpholine/sulfur by the method of Willgerodt to give the corresponding thiomorpholides, hydrolysis to the acetic acids of the formula R—Q—CH$_2$—COOH, conversion into the chlorides of the formula R—Q—CH$_2$—COCl and reaction with ammonia. The halogen compounds of Formula III can be prepared, for example, by reduction of appropriate esters of the formula R—Q—COOalkyl to give the alcohols of the formula R—Q—CH$_2$OH and subsequent reaction with SOCl$_2$, HBr or HI. See, e.g., Houben-Weyl, Methoden der Organischen Chemie (Methods of Organic Chemistry), Fourth Edition, Georg-Thieme-Verlag, Stuttgart, Germany, which disclosures are incorporated by reference herein. The starting materials required for these reactions, in turn, are known or also preparable by fully conventional methods.

The dielectrics of this invention comprise 2 to 15, preferably 3 to 12, components, including at least one acetonitrile of Formula I. The other constituents can be selected from the nematic or nematogenic substances from the classes of azoxybenzenes, benzylideneanilines, biphenyls, terphenyls, phenyl or cyclohexyl benzoates, phenyl or cyclohexyl cyclohexanecarboxylates, phenylcyclohexanes, cyclohexylbiphenyls, cyclohexylcyclohexanes, cyclohexylnaphthalenes, 1,4-biscyclohexylbenzenes, 4,4'-biscyclohexylbiphenyls, phenylpyrimidines or cyclohexylpyrimidines, phenyldioxanes or cyclohexyldioxanes, stilbenes which may be halogenated, benzyl phenyl ethers, tolanes and substituted cinnamic acids.

The most important compounds which can be used as constituents of liquid-crystalline dielectrics of this type can be characterized by Formula IV,

R$^1$—D—B—D—R$^2$    IV wherein each D independently is a carbocyclic or heterocyclic ring system selected from the group comprising 1,4-disubstituted benzene and cyclohexane rings, 4,4'-disubstituted biphenyl, phenylcyclohexane and cyclohexylcyclohexane systems, 2,5-disubstituted pyrimidine and 1,3-dioxane rings, 2,6-disubstituted naphthalene, dihydro- and tetrahydro-naphthlene, quinazoline and tetrahydroquinazoline,

| B is | —CH=CH— | —N(O)=N— |
|---|---|---|
|  | —CH=CY— | —CH=N(O)— |
|  | —C≡C— | —CH$_2$—CH$_2$— |
|  | —CO—O— | —CH$_2$—O— |
|  | —CO—S— | —CH$_2$—S— |

| -continued | |
|---|---|
| —CH=N— | —COO—Ph—COO— | or a C—C single bond, Y is halogen, preferably chlorine, or —CN, and $R^1$ and $R^2$ are alkyl, alkoxy, alkanoyloxy or alkoxycarbonyloxy each having up to 18, preferably up to 8 carbon atoms, or one of these radicals is also —CN, —NC, —NO$_2$, —CF$_3$, F, Cl or Br. In most of these compounds, $R^1$ and $R^2$ are different from one another, one of these radicals usually being an alkyl or alkoxy group. Other variants of the envisaged substituents, however, are also common. Many such substances, or mixtures thereof, are commercially available.

The dielectrics of this invention contain about 0.1 to 60, as a rule at least 5, preferably 10–25 wt. % of the compounds of Formula I. However, the invention also comprises those liquid-crystalline dielectrics to which only less than 5%, for example 0.1 to 3 wt. %, of one or more compounds of Formula I have been added, for example for doping purposes. On the other hand, the compounds of Formula I can account for up to 60% of the dielectrics according to this invention.

The preparation of the dielectrics according to this invention is carried out in a manner conventional per se. As a rule, the desired amount of the components used in a smaller quantity is dissolved in the component representing the main constituent, preferably at an elevated temperature. If a temperature above the clear point of the main constituent is chosen for this, the completeness of the solution process can be observed with particular ease.

The liquid-crystalline dielectrics according to this invention can be modified by suitable additives in such a way that they can be used in all hitherto disclosed types of liquid-crystal display elements.

Additives of this type are known to those skilled in the art and are extensively described in the relevant literature. For example, it is possible to add 0.01–0.5 wt. % of the mentioned conducting salts, preferably ethyldimethyldodecylammonium 4-hexyloxybenzoate; tetrabutylammonium tetraphenylborate or complex salts of crown ethers (compare, for example, I. Haller et al., Mol. Cryst. Liq. Cryst. Volume 24, pages 249–258 (1973)) in order to improve the conductivity; dichroic dyes; or substances for modifying the dielectric anisotropy, the viscosity and/or the orientation of the nematic phases. Substances of these types and their use are described, for example, in German Offenlegungsschriften Nos. 2,209,127, 2,240,864, 2,321,632, 2,338,281, 2,450,088, 2,637,430, 2,853,728 and 2,902,177.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

In the examples, m.p. denotes the melting point and c.p. denotes the clear point of a liquid-crystalline substance.

EXAMPLE 1

180 g of SOCl$_2$ was added to a suspension of 281 g of 4'-pentylbiphenyl-4-ylacetamide [m.p. 185°; obtained by reaction of 4-acetyl-4'-pentylbiphenyl with morpholine/sulfur and subsequent hydrolysis to give 4'-pentylbiphenyl-4-ylacetic acid (m.p. 160°), reaction with SOCl$_2$ to give the chloride and reaction with NH$_3$] in 1 l of toluene at 80°. After stirring at 80° for 6 hours, cooling down and pouring into water, 4'-pentylbiphenyl-4-ylacetonitrile was obtained, m.p. 80°, c.p. −10°.

EXAMPLES 2 TO 46

In analogy to Example 1, the following compounds are obtained by dehydration of the corresponding acetamides:

2. 4'-Methylbiphenyl-4-ylacetonitrile
3. 4'-Ethylbiphenyl-4-ylacetonitrile
4. 4'-Propylbiphenyl-4-ylacetonitrile
5. 4'-Butylbiphenyl-4-ylacetonitrile
6. 4'-(2-Methylbutyl)biphenyl-4-ylacetonitrile
7. 4'-Hexylbiphenyl-4-ylacetonitrile
8. 4'-Heptylbiphenyl-4-ylacetonitrile
9. 4'-Octylbiphenyl-4-ylacetonitrile
10. 4'-(2-Methylheptyl)biphenyl-4-ylacetonitrile
11. 4'-Methoxybiphenyl-4-ylacetonitrile
12. 4'-Ethoxybiphenyl-4-ylacetonitrile
13. 4'-Propoxybiphenyl-4-ylacetonitrile
14. 4'-Butoxybiphenyl-4-ylacetonitrile
15. 4'-Pentyloxybiphenyl-4-ylacetonitrile
16. 4'-Hexyloxybiphenyl-4-ylacetonitrile
17. 4'-Heptyloxybiphenyl-4-ylacetonitrile
18. 4'-Octyloxybiphenyl-4-ylacetonitrile
19. 4'-Formyloxybiphenyl-4-ylacetonitrile
20. 4'-Acetoxybiphenyl-4-ylacetonitrile
21. 4'-Propionyloxybiphenyl-4-ylacetonitrile
22. 4'-Butyryloxybiphenyl-4-ylacetonitrile
23. 4'-Pentanoyloxybiphenyl-4-ylacetonitrile
24. 4'-Hexanoyloxybiphenyl-4-ylacetonitrile
25. 4'-Heptanoyloxybiphenyl-4-ylacetonitrile
26. 4'-Octanoyloxybiphenyl-4-ylacetonitrile
27. 4-(trans-4-Methylcyclohexyl)phenylacetonitrile
28. 4-(trans-4-Ethylcyclohexyl)phenylacetonitrile
29. 4-(trans-4-Propylcyclohexyl)phenylacetonitrile
30. 4-(trans-4-Butylcyclohexyl)phenylacetonitrile
31. 4-(trans-4-Pentylcyclohexyl)phenylacetonitrile, m.p. 53°, c.p. −19°
32. 4-(trans-4-(2-Methylbutyl)cyclohexyl)-phenylacetonitrile
33. 4-(trans-4-Hexylcyclohexyl)phenylacetonitrile
34. 4-(trans-4-Heptylcyclohexyl)phenylacetonitrile
35. 4-(trans-4-Octylcyclohexyl)phenylacetonitrile
36. 4-(trans-4-(1-Methylheptyl)cyclohexyl)-phenylacetonitrile
37. 4'-(trans-4-Methylcyclohexyl)biphenyl-4-ylacetonitrile
38. 4'-(trans-4-Ethylcyclohexyl)biphenyl-4-ylacetonitrile
39. 4'-(trans-4-Propylcyclohexyl)biphenyl-4-ylacetonitrile
40. 4'-(trans-4-Butylcyclohexyl)biphenyl-4-ylacetonitrile
41. 4'-(trans-4-Pentylcyclohexyl)biphenyl-4-ylacetonitrile, m.p. 139°, c.p. 172°
42. 4'-(trans-4-(2-Methylbutyl)cyclohexyl)biphenyl-4-ylacetonitrile 43. 4'-(trans-4-Hexylcyclohexyl)biphenyl-4-ylacetonitrile
44. 4'-(trans-4-Heptylcyclohexyl)biphenyl-4-ylacetonitrile
45. 4'-(trans-4-Octylcyclohexyl)biphenyl-4-ylacetonitrile
46. 4'-(trans-4-(1-Methylheptyl)cyclohexyl)biphenyl-4-ylacetonitrile

EXAMPLE 47

27.9 g of 4-(trans-4-pentylcyclohexyl)benzyl chloride (obtained by chloromethylation of trans-4-pentyl-1-phenylcyclohexane or by esterification of 4-(trans-4-pentylcyclohexyl)benzoic acid, reduction of the methyl or ethyl ester obtained to give 4-(trans-4-pentylcyclohexyl)benzyl alcohol and reaction with $PCl_3$) was added within 15 minutes at 60°, with stirring, to a mixture of 5.5 g of NaCN and 40 ml of dimethyl sulfoxide. The mixture was heated at 70° for 6 hours, cooled down, poured into water and 4-(trans-4-pentylcyclohexyl)phenylacetonitrile was obtained, m.p. 53°, c.p. $-19°$.

The acetonitriles indicated in Examples 1 to 30 and 32 to 46 can be obtained analogously from the corresponding chlorides.

The examples below are of dielectrics according to the invention containing at least one compound of formula I.

EXAMPLE A (a) A mixture of

15% of 4-ethyl-4'-(trans-4-pentylcyclohexyl)biphenyl
30% of 4-ethyl-2'-fluoro-4'-(trans-4-pentylcyclohexyl)biphenyl
23% of 4-pentylphenyl 4-methoxybenzoate
21% of 4-butyl-2-cyanophenyl 4-(trans-4-propylcyclohexyl)benzoate and
11% of 1-(4-(trans-4-pentylcyclohexyl)phenyl)pentan-1,3-dione has the following properties: m.p. $-15°$; c.p. $+96°$; viscosity 56 cSt; and dielectric anisotropy $\Delta\epsilon$-0.5.

After adding 0.1% of ethyldimethyldodecylammonium 4-hexyloxybenzoate, a specific resistance of $1.2 \times 10^9$ Ωcm is obtained. The lower limit of the operating range of temperature is 0° at a frequency of 32 Hz.

(b) The addition of 5% of 4'-pentylbiphenyl-4-ylacetonitrile and 5% of 4-(trans-4-pentylcyclohexyl)biphenyl-4-ylacetonitrile provides a mixture with the following properties: m.p. $-17°$, c.p. $+97°$, viscosity 55 cSt, dielectric anisotropy $\Delta\epsilon$-0.5; specific resistance $4 \times 10^8$ Ωcm; and lower limit of the operating range of temperature $-10°$.

EXAMPLE B (a) A mixture of

15% of trans-1-(4-ethoxyphenyl)-4-propylcyclohexane
10% of trans-1-(4-butoxyphenyl)-4-propylcyclohexane
20% of 4-ethyl-4'-(trans-4-pentylcyclohexyl)biphenyl
5% of 4-(trans-4-pentylcyclohexyl)-4'-(trans-4-propylcyclohexyl)biphenyl
18% of 4-pentylphenyl 4-methoxybenzoate
22% of 4-butyl-2-cyanophenyl 4-(trans-4-propylcyclohexyl)benzoate and
10% of 1-(4-(trans-4-pentylcyclohexyl)phenyl)pentan-1,3-dione has the following properties: m.p. $-10°$; c.p. $+94°$; viscosity 42 cSt; and dielectric anisotropy $\Delta\epsilon$-0.6.

After adding 0.05% of ethyldimethyldodecylammonium 4-hexyloxybenzoate, a specific resistance of $1.1 \times 10^9$ Ωcm is obtained. The lower limit of the operating range of temperature is 0° at a frequency of 32 Hz.

(b) Addition of 10% of 4-(trans-4-pentylcyclohexyl)phenylacetonitrile provides a mixture with the following properties: m.p. $-12°$; c.p. 87°; viscosity 43 cSt; dielectric anisotropy $\Delta\epsilon$-0.5; specific resistance $5 \times 10^8$ Ωcm; and lower limit of the operating range of temperature $-10°$.

The preceding examples can be repeated with similar success by substituting the generically or specifically described reactants and/or operating conditions of this invention for those used in the preceding examples. From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a liquid-crystalline dielectric comprising at least two liquid-crystalline components, the improvement wherein the liquid-crystalline dielectric comprises at least one acetonitrile compound of the formula

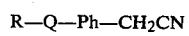
R—Q—Ph—CH₂CN wherein R is alkyl, alkoxy, or alkanoyloxy, each of up to 8 carbon atoms, and Q is 1, 2 or 3 groups, each bonded to one another in the 1- or 4-position and each being a 1,4-phenylene or 1,4-cyclohexylene group, Ph is a 1,4-phenylene group, with the provisos that when Q is 1 of these groups, it is 1,4-cyclohexylene and that R is alkyl when directly attached to a 1,4-cyclohexylene group.

2. A liquid-crystalline dielectric of claim 1 wherein said compound is of the formula

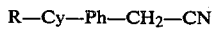
R—Cy—Ph—CH₂—CN wherein Ph is phenylene and Cy is trans-cyclohexylene.

3. A liquid-crystalline dielectric of claim 1 wherein said compound is of the formula

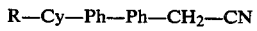
R—Cy—Ph—Ph—CH₂—CN wherein Ph is phenylene and Cy is trans-cyclohexylene.

4. A liquid-crystalline dielectric of claim 1 wherein R is straight-chain alkyl.

5. A liquid-crystalline dielectric of claim 2 wherein R is straight-chain alkyl.

6. A liquid-crystalline dielectric of claim 3 wherein R is straight-chain alkyl.

7. A liquid-crystalline dielectric of claim 1 wherein R is straight-chain alkoxy.

8. A liquid-crystalline dielectric of claim 1 wherein R is straight-chain $C_{3-5}$-alkyl.

9. A liquid-crystalline dielectric of claim 1 wherein the amount of said acetonitrile is 0.1 to 60 wt. %.

10. A liquid-crystalline dielectric of claim 1 further comprising an amount of a dissolved conducting salt suitable for use in liquid-crystalline dielectrics to influence the conductivity thereof.

11. An electro-optical display element comprising a liquid crystal cell containing a dielectric of claim 1.

12. A liquid-crystalline dielectric of claim 1 wherein said compound is of the formula R—Ph—Ph—Ph—CH₂CN R—Ph—Cy—Ph—CH₂CN R—Cy—Cy—Ph—CH₂CN R—Ph—Ph—Ph—Ph—CH₂CN R—Ph—Ph—Cy—Ph—CH₂CN R—Ph—Cy—Ph—Ph—CH₂CN R—Ph—Cy—Cy—Ph—CH₂CN R—Cy—Ph—Ph'Ph—CH₂CN R—Cy—Ph—Cy—Ph—CH₂CN R—Cy—Cy—Ph—Ph—CH₂CN or R—Cy—Cy—Cy—Ph—CH₂CN.

13. A liquid-crystalline dielectric of claim 1 wherein Q is 2 groups.

14. A liquid-crystalline dielectric of claim 1 wherein Q is 3 groups.

* * * * *